(12) United States Patent
DeMeo et al.

(10) Patent No.: US 8,816,115 B2
(45) Date of Patent: Aug. 26, 2014

(54) METAL NANOPARTICLES

(75) Inventors: Ronald F. DeMeo, Fort Lauderdale, FL (US); James Adam Bradshaw, Knoxville, TN (US); Federico Polo, Castelcucco (IT)

(73) Assignee: Meridian Research and Development, Fort Lauderdale, FL (US)

( * ) Notice: Subject to any disclaimer, the term of this patent is extended or adjusted under 35 U.S.C. 154(b) by 0 days.

(21) Appl. No.: 13/266,755

(22) PCT Filed: Apr. 2, 2010

(86) PCT No.: PCT/US2010/029863
§ 371 (c)(1),
(2), (4) Date: May 17, 2012

(87) PCT Pub. No.: WO2010/115159
PCT Pub. Date: Oct. 7, 2010

(65) Prior Publication Data
US 2012/0223258 A1    Sep. 6, 2012

Related U.S. Application Data

(60) Provisional application No. 61/166,626, filed on Apr. 3, 2009.

(51) Int. Cl.
*C07F 7/00* (2006.01)
*B32B 5/16* (2006.01)

(52) U.S. Cl.
USPC .............................. 556/81; 428/402

(58) Field of Classification Search
USPC .............................. 556/81; 428/402
See application file for complete search history.

(56) References Cited

U.S. PATENT DOCUMENTS

| | | | |
|---|---|---|---|
| 4,421,847 A | 12/1983 | Jung et al. | |
| 4,877,724 A | 10/1989 | Chen et al. | |
| 6,841,791 B2 | 1/2005 | DeMeo et al. | |
| 7,410,650 B2 | 8/2008 | Lin | |
| 7,476,889 B2 | 1/2009 | DeMeo et al. | |
| 7,678,359 B2 | 3/2010 | Chung et al. | |
| 2008/0020317 A1* | 1/2008 | Park et al. | 430/138 |

OTHER PUBLICATIONS

Cotton and Wilkinson, Advanced Inorganic Chemistry, 5th edition, 1988, Wiley, chapters 19 and 25.*
Koltypin et al., J. Mater. Chem., 2002, 12, 1107-1110.*
Pinson, Jean et al., "Attachment of organic layers to conductive or semiconductive surfaces by reduction of diazonium salts," *Chem. Soc. Rev.* (2005) 34, pp. 429-439.
Liu, Guozhen et al., "Diazonium salts: Stable monolayers on gold electrodes for sensing applications," *Journal of Electroanalytical Chemistry* 600 (2007) pp. 335-344.
Mirkhalaf, Fakhradin et al., "Synthesis of Metal Nanoparticles Stabilized by Megal-Carbon Bonds," *J. Am. Chem Soc.*, (2006) 128, pp. 7400-7401.

* cited by examiner

*Primary Examiner* — Porfirio Nazario Gonzalez
*Assistant Examiner* — Kofi Adzamli
(74) *Attorney, Agent, or Firm* — Sideman & Bancroft LLP.; Guy W. Chambers

(57) ABSTRACT

Provided herein are metal nanoparticles, metal nanopowders, methods of synthesizing the same, and radiation shields using the same.

23 Claims, 4 Drawing Sheets

METAL NANOPARTICLES

CROSS-REFERENCE TO RELATED APPLICATIONS

This application claims priorities of Patent Cooperation Treaty Application No. PCT/US2010/029863, filed on Apr. 2, 2010, and Provisional Application No. 61/166,626, filed Apr. 3, 2009, the disclosures of which are incorporated herein by reference in their entirety for all purposes.

BACKGROUND OF THE INVENTION

Exposure to ionizing radiation is considered to be dangerous for humans. The rays or particles can do damage to human tissue to an extent that is dose dependent: the more radiation, the more damage. One theory on the relationship between absorbed radiation dose and the probability of health effects is that it is approximately linear without threshold, which would mean that there is a possible risk of health effects with any dose, however small. While there may indeed be no absolutely safe dose, there are dosages that are considered acceptable for practical purposes and unlikely to produce health effects. The risk of exposure is also dependent to a certain degree on the length of time over which the exposure occurred. The body can tolerate small doses that add up over time better than the same exposure all at once.

All humans are exposed to some radiation simply by living on earth. This naturally occurring or so-called background radiation comes from the radioactive decay of naturally occurring radioactive elements in the earth's crust. In addition to this, other sources of radiation are part of the course of everyday life such as dental or medical X rays, microwave radiation, luminous watch dials, color televisions, cosmic radiation, smoke alarms, and exit signs. A variety of sources of exposure to extremely small doses which add up slowly over time since dosage of radiation is cumulative over a lifetime.

The most commonly known destructive application of radiation is atomic bombs and/or military applications of radiation. Another commonly known application is atomically/nuclear fueled power generation. The electromagnetic radiation released by an atomic bomb, covering more-or-less the entire electromagnetic spectrum, can penetrate deeply into human tissue to damage human cells. The threat posed by atomic bombs has arguably increased in recent years with the growth of terrorism and the very real possibility that a "dirty bomb" can be made by terrorists through use of readily available nuclear waste and commercial application materials. Another source of concern comes from nuclear power generation, which produces byproducts dangerous to the public and surrounding environment as well as providing an additional route for supply of radioactive materials to terrorist organizations. The destructive threat to humanity of such nuclear bombs has given rise to a need for cost-effective radiation protection, including the need for lightweight radiation protective garments. Ideally, such lightweight radiation protective garments would simultaneously provide protection against other types of hazards, such as fire, chemical, biological, projectile hazards and other forms of electromagnetic radiation. In this way, first responders, such as firemen, paramedics, policemen or the military (and aerospace) could use a single garment to provide them with protection against any type of hazard they might foreseeably confront. Broad-spectrum portable/mobile protection, such as, but not limited to, hybrid radiation-ballistics protection has, until now, not been feasible due to, but not limited to, weight and financial resource limitations as well as a lack in available technology. Such "universal" protective garments are also addressed in Applicants' application Ser. No. 10/620,954, filed Jul. 16, 2003, entitled "Multiple Hazard Protection Articles And Methods For Making Them", the disclosure of which is incorporated herein by reference in its entirety for all purposes.

A number of constructive uses have also been developed for harnessing radiation. These constructive uses include, but are not limited to, medical x-rays diagnostics, nuclear power generation, and radiation based material and structural analysis found in fundamental and applied sciences and engineering. Presumably, many other constructive uses of radiation remain undiscovered.

When an exposure occurs over an extended period of time, it is referred to as "chronic exposure." Chronic exposure to radiation may occur naturally and in the course of daily life. Persons working in the nuclear industry or utilizing a radiation source in the course of their work receive additional exposure. Standards have been set to protect such workers from dangerous dosages of radiation. However, these standards tend to change (lower) as more is learned about the effects of radiation on the human body. A principal exists in the field of radiation protection, which is referred to by the acronym "ALARA", which stands for As Low As Reasonably Achievable. Under this principle all exposures are kept to standardized minimum. In addition, the industry is required to take measures to reduce exposure if they can do so at a reasonable cost. In order to monitor occupational exposures, the worker wears a film badge or "dosimeter" to measure the amount of radiation to which they are exposed. Records are kept of the readings so that cumulative dose tabulation can be kept. Recent recommendations have resulted in a lowering of the maximum acceptable exposure. As indicated by the Uranium Institute, "Dose limits are considered to be the maximum acceptable exposure for an individual but they do not represent an acceptable level of exposure for a large number of individuals, or a level of exposure to which an individual can be repeatedly exposed."

There are numerous international, federal and private organizations that disagree on how much exposure is "unhealthy". Some feel that any dose of ionizing radiation, no matter how small, has the potential to do cellular damage. Others believe that there is not enough evidence to support such claims. One common agreement, however, is that there is no one standard physiological reaction to specific levels of radiation. Some people are able to tolerate certain types of radiation better than others. Persons exposed to the same sources of "acute" (short-term) radiation can end up later in life with very different physiological results. Ultimately, it is important for those concerned to investigate all current avenues of research and keep radiation exposure to an absolute minimum. DeMeo and others have described the incorporation of radiaopaque materials and non-woven fibers (see; U.S. Pat. No. 7,476,889; incorporated hereby by reference in its entirety). Furthermore, advanced techniques in extrusion and compounding allowed the higher loading of these radiopaque compounds to create a flexible garment. It is understood that the more dense and thinner the material, the more efficient it is in attenuating radiation. In order to increase the load of radiopaque materials in filaments, films, and fabrics, DeMeo had incorporated nano-metals as described in U.S. Pat. No. 7,476,889. Although this allowed for better radiation attenuation, the cost of the materials and the limited supply limits their applications.

Typical nano-metal manufacturing involves techniques as described in the art, e.g., in U.S. Patent Appl. No. 2008/0226535, U.S. Pat. No. 7,410,650 and U.S. Pat. No. 7,678, 359. In all of these processes, the nano-metal is made from the anatomic level and built upward to create a nano-metal. Further, the processes described in these references are not scalable in that yield is quite low and thus, economically, not practicable. The instant application describes the first process to manufacture nano-metals from the macro level downward. As described further herein, in some embodiments, Applicants' methods comprise providing, e.g., a bulk compound, such as tungsten (W) and then convert it directly to mono dispersed chemical product (nano metal). In doing so, large amounts of metal nanoparticles can be made in a commercial scale and at a fraction of the cost.

Thus, there is a need in the art for compositions useful for radiation protection. The compositions and methods provided herein meet these and other needs in the art.

In addition human and assorted biological protection needs from various forms of radiation, there are multiple other areas where radiation attenuation is desirable. Various electronic systems, be it land, air, sea, and space based, are known to be particularly sensitive to radiation that can cause errors in functionality as well as partial or total system failure. Componentry critical to research, medical treatment, as well as defense systems require controlled isolation from various radiation sources and thus provide an additional demand for materials advancement.

SUMMARY OF THE INVENTION

In one aspect, a metal nanoparticle is provided including a metal core and an outer layer encompassing the metal core. The outer layer includes a plurality of organic substituents bonded to the metal core. The metal nanoparticle typically is less than 1 μm in length in all dimensions.

In another aspect, a metal nanopowder is provided. The metal nanopowder includes a plurality of the metal nanoparticles having a metal core and an outer layer encompassing the metal core. The outer layer includes a plurality of organic substituents bonded to the metal core. The metal nanoparticle is typically less than 1 μm in length in all dimensions.

In another aspect, radiation shields are provided. The radiation shield includes a metal nanoparticle having a metal core and an outer layer encompassing the metal core. The outer layer includes a plurality of organic substituents bonded to the metal core. The metal nanoparticle is typically less than 1 μm in length in all dimensions.

In another aspect, a method is provided for making a metal nanoparticle. The method includes contacting a metal with a diazonium compound substituted with an organic substituent. The metal is allowed to react with the diazonium compound thereby forming a metal nanoparticle. The metal nanoparticle includes a metal core and an outer layer encompassing the metal core. The outer layer includes a plurality of the organic substituents bonded to the metal core.

Some embodiments of the present invention are set forth in claim format directly below:

Claim 1. A metal nanoparticle comprising a metal core and an outer layer encompassing said core, said outer layer comprising a plurality of organic substituents bonded to said metal core, wherein said metal nanoparticle is less than 1 μm in length in all dimensions.

Claim 2. The metal nanoparticle according to claim 1, wherein said metal core comprises
  (i) a metal selected from the group consisting of germanium, antimony, polonium, tellurium, scandium, yttrium, lanthanum, actinium, titanium, zirconium, hafnium, rutherfordium, niobium, dubnium, chromium, molybdenum, seaborgium, manganese, technetium, rhenium, bohrium, ruthenium, osmium, hassium, cobalt, rhodium, iridium, meitnerium, palladium, platinum, darmstadtium, copper, silver, roentgenium, zinc, cadmium, mercury, indium, gallium, thallium, ununbium, tungsten, gold, aluminum, bismuth, iron, vanadium, nickel, palladium, tin, lead, tantalum and uranium; or
  (ii) a metal selected from the group consisting of tungsten, germanium, gold, aluminum, bismuth, iron, vanadium, silver, nickel, palladium, tin, lead, tantalum, copper, and uranium.

Claim 3. The metal nanoparticle according to claim 1, wherein said metal core comprises
  (i) gold;
  (ii) silver;
  (iii) aluminum;
  (iv) iron;
  (v) iron-oxide;
  (vi) copper;
  (vii) germanium; or
  (viii) tungsten.

Claim 4. The metal nanoparticle according to any one of claims 1 to 3, wherein said plurality of organic substituents are
  (i) covalently bonded to said metal core through a carbon-metal covalent bond; or
  (ii) crosslinked.

Claim 5. The metal nanoparticle according to any one of claims 1 to 4, wherein said plurality of organic substituents form a self-assembled monolayer.

Claim 6. The metal nanoparticle according to any one of claims 1 to 5, wherein said plurality of organic substituents
  (i) are selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
  (ii) are selected from the group consisting of $R^1$-substituted or unsubstituted alkyl, $R^1$-substituted or unsubstituted heteroalkyl, $R^1$-substituted or unsubstituted cycloalkyl, $R^1$-substituted or unsubstituted heterocycloalkyl, $R^1$-substituted or unsubstituted aryl, and $R^1$-substituted or unsubstituted heteroaryl;
    wherein $R^1$ is halogen, $-CN$, $-S(O)_nR^2$, $-NR^3R^4$, $-C(O)R^5$, $-NR^6-C(O)R^7$, $-NR^8-C(O)-OR^9$, $-C(O)NR^{10}R^{11}$, $-NR^{12}S(O)_2R^{13}$, $-OR^{14}$, $-S(O)_2NR^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl, wherein n is an integer from 0 to 2; and
    $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl.

Claim 7. The metal nanoparticle according to any one of claims 1 to 5, wherein said plurality of organic substituents have the formula:

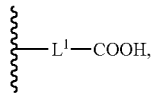

wherein

L$^1$ is R$^1$-substituted or unsubstituted alkylene, R$^1$-substituted or unsubstituted heteroalkylene, R$^1$-substituted or unsubstituted cycloalkylene, R$^1$-substituted or unsubstituted heterocycloalkylene, R$^1$-substituted or unsubstituted arylene, and R$^1$-substituted or unsubstituted heteroarylene;

R$^1$ is halogen, —CN, —S(O)$_n$R$^2$, —NR$^3$R$^4$, —C(O)R$^5$, —NR$^6$—C(O)R$^7$, —NR$^8$—C(O)—OR$^9$, —C(O)NR$^{10}$R$^{11}$, —NR$^{12}$S(O)$_2$R$^{13}$, —OR$^{14}$, S(O)$_2$NR$^{15}$, R$^{16}$-substituted or unsubstituted alkyl, R$^{16}$-substituted or unsubstituted heteroalkyl, R$^{16}$-substituted or unsubstituted cycloalkyl, R$^{16}$-substituted or unsubstituted heterocycloalkyl, R$^{16}$-substituted or unsubstituted aryl, or R$^{16}$-substituted or unsubstituted heteroaryl, wherein n is an integer from 0 to 2, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$ and R$^{16}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

Claim 8. The metal nanoparticle according to claim 7, wherein L$^1$ is (i) R$^1$-substituted or unsubstituted alkylene;
(ii) R$^1$-substituted or unsubstituted C$_1$-C$_{20}$ alkylene;
(iii) R$^1$-substituted or unsubstituted C$_1$-C$_{10}$ alkylene;
(iv) R$^1$-substituted or unsubstituted C$_1$-C$_5$ alkylene;
(v) R$^1$-substituted or unsubstituted C$_1$-C$_3$ alkylene; or
(vi) unsubstituted C$_1$-C$_3$ alkylene.

Claim 9. The metal nanoparticle according to any one of claims 1 to 8, wherein said plurality of organic substituents are identical.

Claim 10. The metal nanoparticle according to any one of claims 1 to 9, wherein said metal nanoparticle is (i) less than 50 nm in length in all dimensions;
(ii) less than 25 nm in length in all dimensions;
(iii) less than 10 nm in length in all dimensions;
(iv) less than 5 nm in length in all dimensions; or
(v) less than 3 nm in length in all dimensions.

Claim 11. A metal nanopowder comprising a plurality of metal nanoparticles wherein a metal nanoparticle is a metal nanoparticle according to any one of claims 1 to 10.

Claim 12. A radiation shield comprising a plurality of metal nanoparticles wherein a metal nanoparticle is a metal nanoparticle according to any one of claims 1 to 10.

Claim 13. A radiation shield comprising a metal nanoparticle, said metal nanoparticle comprising a metal core and an outer layer encompassing said core, said outer layer comprising a plurality of organic substituents covalently bonded to said metal core, wherein said metal nanoparticle is less than 1 µm in length in all dimensions.

Claim 14. The radiation shield according to any one of claims 12 to 13, wherein said radiation shield is lead-free.

Claim 15. The radiation shield according to any one of claims 12 to 14, wherein said radiation shield is a personal radiation shield.

Claim 16. The radiation shield of claim 15, wherein said personal radiation shield is used to shield radiation from a cell phone, a medical device, or a shielding for equipment and use in aerospace;

(ii) is a blanket, head covering, foot covering, hand covering, an undergarment, an injection molded product, or an extruded product; or
(iii) comprises a non-woven material, a fiber material, a film, a filament, or a woven material.

Claim 17. A method of making a plurality of metal nanoparticles, said method comprising the steps of:

(a) contacting a metal with a diazonium compound substituted with an organic substituent; and
(b) allowing the metal to react with the diazonium compound thereby forming a metal nanoparticle wherein said metal nanoparticle comprises a metal core and an outer layer encompassing said core, said outer layer comprising a plurality of said organic substituents covalently bonded to said metal core, wherein at least 50% of said plurality of metal nanoparticles are less than 1 µm in length in all dimensions.

Claim 18. The method according to claim 17, wherein a plurality of metal nanoparticle are produced, and wherein (i) at least 60% of said plurality of metal nanoparticles are less than 100 nm in length in all dimensions;
(ii) at least 70% of said plurality of metal nanoparticles are less than 100 nm in length in all dimensions;
(iii) at least 80% of said plurality of metal nanoparticles are less than 100 nm in length in all dimensions;
(iv) at least 90% of said plurality of metal nanoparticles are less than 100 nm in length in all dimensions;
(v) at least 95% of said plurality of metal nanoparticles are less than 100 nm in length in all dimensions; or
(vi) 100% of said plurality of metal nanoparticles are less than 100 nm in length in all dimensions.

Claim 19. The method according to any one of claims 18 to 19, wherein said metal and said metal core (i) comprise a metal selected from the group consisting of tungsten, germanium, gold, aluminum, bismuth, iron, vanadium, silver, nickel, palladium, tin, lead, tantalum, copper, and uranium; or
(ii) consist of tungsten.

Claim 20. The method according to any one of claims 17 to 19, wherein said metal comprises tungsten.

Claim 21. The method according to any one of claims 17 to 20, wherein said plurality of organic substituents (i) are covalently bonded to said metal core through a carbon-metal covalent bond; or
(ii) crosslinked.

Claim 22. The method according to any one of claims 17 to 21, wherein said plurality of organic substituents (i) are selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
(ii) are selected from the group consisting of R$^1$-substituted or unsubstituted alkyl, R$^1$-substituted or unsubstituted heteroalkyl, R$^1$-substituted or unsubstituted cycloalkyl, R$^1$-substituted or unsubstituted heterocycloalkyl, R$^1$-substituted or unsubstituted aryl, and R$^1$-substituted or unsubstituted heteroaryl;

wherein R¹ is halogen, —CN, —S(O)$_n$R², —NR³R⁴, —C(O)R⁵, —NR⁶—C(O)R⁷, —NR⁸—C(O)—OR⁹, —C(O)NR¹⁰R¹¹, —NR¹²S(O)₂R¹³, —OR¹⁴, —S(O)₂NR¹⁵, R¹⁶-substituted or unsubstituted alkyl, R¹⁶-substituted or unsubstituted heteroalkyl, R¹⁶-substituted or unsubstituted cycloalkyl, R¹⁶-substituted or unsubstituted heterocycloalkyl, R¹⁶-substituted or unsubstituted aryl, or R¹⁶-substituted or unsubstituted heteroaryl, wherein n is an integer from 0 to 2; and R², R³, R⁴, R⁵, R⁶, R⁷, R⁸, R⁹, R¹⁰, R¹¹, R¹², R¹³, R¹⁴, R¹⁵ and R¹⁶ are independently hydrogen, unsubstituted alkyl, unsubstituted heteroalkyl, unsubstituted cycloalkyl, unsubstituted heterocycloalkyl, unsubstituted aryl, or unsubstituted heteroaryl.

Claim 23. The method according to any one of claims 17 to 21, wherein said plurality of organic substituents have the formula:

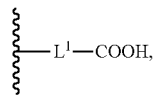

wherein

L¹ is R¹-substituted or unsubstituted alkylene, R¹-substituted or unsubstituted heteroalkylene, R¹-substituted or unsubstituted cycloalkylene, R¹-substituted or unsubstituted heterocycloalkylene, R¹-substituted or unsubstituted arylene, and R¹-substituted or unsubstituted heteroarylene;

R¹ is halogen, —CN, —S(O)$_n$R², —NR³R⁴, —C(O)R⁵, —NR⁶—C(O)R⁷, —NR⁸—C(O)—OR⁹, —C(O)NR¹⁰R¹¹, NR¹²S(O)₂R¹³, OR¹⁴, —S(O)₂NR¹⁵, R¹⁶-substituted or unsubstituted alkyl, R¹⁶-substituted or unsubstituted heteroalkyl, R¹⁶-substituted or unsubstituted cycloalkyl, R¹⁶-substituted or unsubstituted heterocycloalkyl, R¹⁶-substituted or unsubstituted aryl, or R¹⁶-substituted or unsubstituted heteroaryl, wherein n is an integer from 0 to 2, R², R³, R⁴, R⁵, R⁶, R⁷, R⁸, R⁹, R¹⁰, R¹¹, R¹², R¹³, R¹⁴, R¹⁵ and R¹⁶ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Claim 24. The method according to claim 23, wherein L1 is
(i) R¹-substituted or unsubstituted alkylene;
(ii) R¹-substituted or unsubstituted C₁-C₂₀ alkylene;
(iii) R¹-substituted or unsubstituted C₁-C₁₀ alkylene;
(iv) R¹-substituted or unsubstituted C₁-C₅ alkylene;
(v) R¹-substituted or unsubstituted C₁-C₃ alkylene; or
(vi) unsubstituted C₁-C₃ alkylene.

Claim 25. The method according to any one of claims 17 to 24, wherein said plurality of organic substituents are identical.

Claim 26. The method according to any one of claims 17 to 25, wherein at least 90% of said plurality of metal nanoparticles is
(i) less than 50 nm in length in all dimensions;
(ii) less than 25 nm in length in all dimensions;
(iii) less than 10 nm in length in all dimensions;
(iv) less than 5 nm in length in all dimensions; or
(v) less than 3 nm in length in all dimensions.

DETAILED DESCRIPTION OF THE INVENTION

I. Definitions

Figure 1:
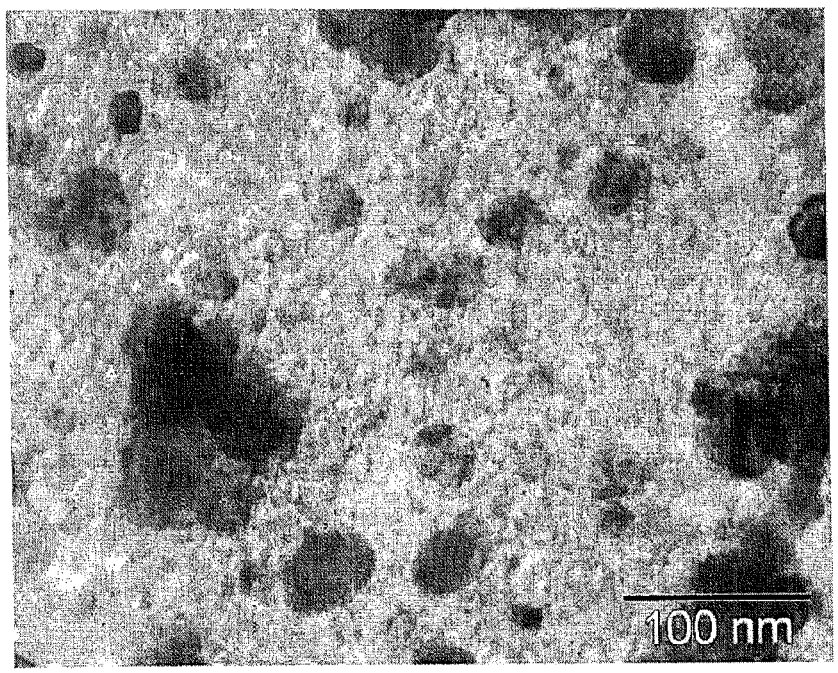
FIG. 1 depicts a TEM image of one form of a metal powder fabricated according to the invention. Details are described in Example 1.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S(O$_2$)—R', where R' is an alkyl group as defined above. R' may have a specified number of carbons (e.g. "C$_1$-C$_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "biological subject," as used herein, refers to living subjects and encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

By "contacting" is meant an instance of exposure of at least one substance to another substance. As used herein, the term "contacting" includes reference to placement of one substance in direct physical association with another substance. Further, the term "contacting" is used herein interchangeably with the following: combined with, added to, mixed with, passed over, incubated with, flowed over, etc.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may, but need not, be present, and the description includes situations where the heterocyclo group is mono- or disubstituted with an alkyl group and situations where the heterocyclo group is not substituted with the alkyl group. "Optionally substituted" means a ring, which is optionally substituted independently with substituents. For example, a site of a group that is unsubstituted may be substituted with hydrogen.

The symbol ⌇ denotes a point of attachment of a moiety to the remainder of a compound or composition.

II. Metal Nanoparticles

In one aspect, a metal nanoparticle is provided including a metal core and an outer layer encompassing the metal core. The outer layer includes a plurality of organic substituents bonded to the metal core. The metal nanoparticle typically is less than 1 μm in length in all dimensions. For example, where the metal nanoparticle is approximately spherical, the longest diameter is less than 1 μm. In some embodiments, the metal nanoparticle is less than 200 nm in length in all dimensions.

In some embodiments, the outer layer includes a plurality of organic substituents bonded to the metal core. In some embodiments the outer layer includes a plurality of organic substituents bonded to the metal core through a covalent bond, an ionic bond, a hydrogen bond, or hydrophobic forces. In certain embodiments, the outer layer includes a plurality of organic substituents covalently bonded to the metal core.

The metal core includes a metal. The metal may be germanium, antimony, polonium, tellurium, scandium, yttrium, lanthanum, actinium, titanium, zirconium, hafnium, rutherfordium, niobium, dubnium, chromium, molybdenum, seaborgium, manganese, technetium, rhenium, bohrium, ruthenium, osmium, hassium, cobalt, rhodium, iridium, meitnerium, palladium, platinum, darmstadtium, copper, silver, roentgenium, zinc, cadmium, mercury, indium, gallium, thallium, ununbium, tungsten, gold, aluminum, bismuth, iron, vanadium, nickel, palladium, tin, lead, tantalum, or uranium. In some embodiments, the metal is tungsten, germanium, gold, aluminum, bismuth, iron, vanadium, silver, nickel, palladium, tin, lead, tantalum, copper, or uranium. In some embodiments, the metal is gold. In some embodiments, the metal is silver. In some embodiments, the metal is aluminum. In some embodiments, the metal is iron. In some embodiments, the metal is iron-oxide. In some embodiments, the metal is copper. In some embodiments, the metal is germanium. In some embodiments, the metal is tungsten.

The metal core may include or entirely consist of any one of the metals described in the preceding paragraph. In some embodiments, the metal core is a gold core. In some embodiments, the metal core is a silver core. In some embodiments, the metal core is an aluminum core. In some embodiments, the metal core is an iron core. In some embodiments, the metal core is an iron-oxide core. In some embodiments, the metal core is a copper core. In some embodiments, the metal core is a germanium core. In some embodiments, the metal core is a tungsten core. The metal core may be of any appropriate shape. In some embodiments, the metal core is spherical. In some embodiments, the metal core is cylindrical. In some embodiments, the metal core is approximately spherical. In some embodiments, the metal core is approximately cylindrical.

In some embodiments, a metal core includes or entirely consists of an alloy or oxide cluster, such as Ni$_3$Nb, super alloy inconel, steel, or oxide species such as Fe$_2$O$_3$ and Fe$_3$O$_4$. In some embodiments, a metal core includes or entirely consists of a metal sulfide, such as AuS. In some embodiments, a metal core is a non-singular component system, such as Ni$_3$Nb, super alloy inconel, steel, oxide (e.g. Fe$_2$O$_3$ and Fe$_3$O$_4$) or a multiple component system having two or more component multiple shell model such as a gold core surrounded with a silver layer, various tungsten carbide species, as well as metal-ceramic mixtures. In some embodiments, two or more structurally differing variations of the same material such as crystalline and non-crystalline $Al_2O_3$ and other similar chemical species may be present.

The metal core includes an outer surface. In some embodiments, the outer surface is composed of a metal selected from those described above. The outer surface of the metal core is typically in contact with the outer layer of the metal nanoparticle. Thus, in some embodiments, the plurality of organic substituents, forming at least in part the outer layer, are covalently bonded to the metal core (e.g. the outer surface of the metal core) through a carbon-metal covalent bond. As described in more detail below, one or more organic substituents forming the plurality of organic substituents may be crosslinked.

In some embodiments, the organic substituents comprise, at least in part, a self-assembled monolayer. Thus, the plurality of organic substrates may form a single layer of molecules encompassing the metal core as the outer layer of the metal nanoparticle.

One or more, or all, of the plurality of organic substituents may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the organic substituent is selected from $R^1$-substituted or unsubstituted alkyl, $R^1$-substituted or unsubstituted heteroalkyl, $R^1$-substituted or unsubstituted cycloalkyl, $R^1$-substituted or unsubstituted heterocycloalkyl, $R^1$-substituted or unsubstituted aryl, or $R^1$-substituted or unsubstituted heteroaryl. $R^1$ is halogen, —CN, —S(O)$_n$R$^2$, —NR$^3$R$^4$, —C(O)R$^5$, —NR$^6$—C(O)R$^7$, —NR$^8$—C(O)—OR$^9$, —C(O)NR$^{10}$R$^{11}$, —NR$^{12}$S(O)$_2$R$^{13}$, —OR$^{14}$, —S(O)$_2$NR$^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl, wherein n is an integer from 0 to 2. $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, one or more, or all, of the plurality of organic substituents have the formula:

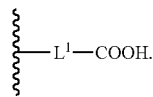

(I)

In Formula (I), $L^1$ is $R^1$-substituted or unsubstituted alkylene, $R^1$-substituted or unsubstituted heteroalkylene, $R^1$-substituted or unsubstituted cycloalkylene, $R^1$-substituted or unsubstituted heterocycloalkylene, $R^1$-substituted or unsubstituted arylene, and $R^1$-substituted or unsubstituted heteroarylene. $R^1$ is halogen, —CN, —S(O)$_n$R$^2$, —NR$^3$R$^4$, —C(O)R$^5$, —NR$^6$—C(O)R$^7$, —NR$^8$—C(O)—OR$^9$, —C(O)NR$^{10}$R$^{11}$, —NR$^{12}$S(O)$_2$R$^{13}$, —OR$^{14}$, —S(O)$_2$NR$^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl, wherein n is an integer from 0 to 2. $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments, $L^1$ is $R^1$-substituted or unsubstituted alkylene. $L^1$ may also be $R^1$-substituted or unsubstituted $C_1$-$C_{20}$ alkylene. Alternatively, $L^1$ is $R^1$-substituted or unsubstituted $C_1$-$C_{10}$ alkylene. In other embodiments, $L^1$ is $R^1$-substituted or unsubstituted $C_1$-$C_5$ alkylene. $L^1$ may also be $R^1$-substituted or unsubstituted $C_1$-$C_3$ alkylene. Or $L^1$ is unsubstituted $C_1$-$C_3$ alkylene.

In some embodiments, one or more (i.e., at least two), or all, of the plurality of organic substituents include a substituted or unsubstituted porphyrin optionally bound to a porphyrin metal. The porphyrin metal is a metal ion typically with a charge of 2+ or 3+ and is capable of binding within the central N4 cavity formed by the loss of two protons of the porphyrin. In some embodiments, the porphyrin metal is magnesium ion, nickel ion, or manganese ion. In some related embodiments, one or more (i.e., at least two), or all, of the plurality of organic substituents are a substituted or unsubstituted porphyrin optionally bound to a porphyrin metal.

As described above, in some embodiments, the plurality of organic substituents is different, i.e., the plurality of organic substituents comprises different members. In some embodiments, the plurality of organic substituents is identical, i.e., the plurality of organic substituents comprises identical members. In some embodiments, some portion(s) of the organic substituents differ. As used herein, the terms "different" or "differ" mean not the same, not of the same identity.

In some embodiments, each substituted group described above for the organic substituent is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted, substituted heteroalkylene, substituted arylene, and/or substituted heteroarylene described above in the organic substituents are substituted with at least one substituent group. In other embodiments, at least one or all of these groups are substituted with at least one size-limited substituent group. Alternatively, at least one or all of these groups are substituted with at least one lower substituent group.

In other embodiments of the organic substituent, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

In some embodiments, the metal nanoparticle is less than 200 nm in length in all dimensions. In some embodiments, the metal nanoparticle is less than 100 nm in length in all dimensions. In some embodiments, the metal nanoparticle is less than 50 nm in length in all dimensions. In other embodiment, the metal nanoparticle is less than 25 nm in length in all dimensions. The metal nanoparticle may also be less than 10 nm in length in all dimensions. In still other embodiments, the metal nanoparticle is less than 5 nm in length in all dimensions. Or the metal nanoparticle is less than 3 nm in length in all dimensions. In some embodiments, the metal nanoparticle is from about 1 μm to about 3 nm in length in all dimensions. In some embodiments, the metal nanoparticle is from about 200 nm to about 5 nm in length in all dimensions. In some embodiments, the metal nanoparticle is from about 100 nm to about 10 nm in length in all dimensions. In some embodiments, the metal nanoparticle is from about 50 nm to about 25 nm in length in all dimensions. In some embodiments, the metal nanoparticle is from about 50 nm to about 10 nm in length in all dimensions.

In some embodiments, the metal nanoparticle has the formula

$$M\text{-}L^1\text{-}COOH \quad (II).$$

In Formula (II), $L^1$ is as defined above and M is a metal as defined above.

In some embodiments, the organic substituents covalently bonded to the metal may be crosslinked. Crosslinking reactions are well known in the art. Crosslinking of the organic substituents typically require that reactive functional groups be attached to the organic substituents. The reactive functional groups can then be subjected to crosslinking conditions that allow covalent bond formation at the reactive functional group site of different organic substituents on a metal core to facilitate crosslinking. In some embodiments, the crosslinking conditions include the use of a crosslinking agent. Thus, in some embodiments, the metal nanoparticle has the formula:

$$M\text{-}L^1\text{-}R^{18} \quad (III).$$

In Formula (III), $R^{18}$ is a reactive functional group. M and $L^1$ are as defined above.

A useful crosslinking agent can react with a reactive functional group such as, for example, an amine, sulfhydryl, carboxylic acid, or aldehyde group attached to an organic substituent as described above. The residues of certain useful crosslinking agents, such as, for example, difunctional gelatin hardeners, bisepoxides and bisisocyanates become a part of a linking group in a crosslink between organic substituents covalently bonded to a metal, which is formed as a result of the crosslinking reaction.

Other useful crosslinking agents facilitating the crosslinking include, for example, as consumable catalysts, and are not present in the final conjugate. Examples of such crosslinking agents are carbodiimide and carbamoylonium crosslinking agents as disclosed in U.S. Pat. No. 4,421,847, and the dication ethers of U.S. Pat. No. 4,877,724, the disclosures of which are hereby incorporated herein by reference in their entirety for all purposes. With these crosslinking agents, one of the reactive functional groups is typically a carboxyl group and the other typically an amine or sulfhydryl group.

Additional reactive functional groups include, for example, semicarbazido; thiocarbazido; thiosemicarbazido; isocyanato and isothiocyanato; vinyl sulfonylalkyloxy; vinyl sulfonylalkylpoly(oxyalkyl)oxy, such poly(oxyalkyl) portion preferably comprising a poly(oxyethylene) group or a poly(oxyethylene)-co-poly(oxypropylene) copolymer group; amidatoalkyloxy; hydrazidoalkyloxy; azidocarbonylalkyloxy; aryloxycarbonyloxyalkyloxy; aryloxycarbonyl(polyoxyalkyl)oxy, such poly(oxyalkyl) portion preferably comprising a poly(oxyethylene) group or a poly(oxyethylene)-co-poly(oxypropylene) copolymer group; triazines such as 4,6-dichloro-2-triazinylamino, 4,6-dichloro-2-triazinyloxy, 4,6-dichlorotriazinyl-2-oxy(polyalkyloxy), 4-alkoxy-6-chloro-2-triazinyloxy, and 4-alkoxy-6-chloro-2-triazinyl(polyoxyalkyl)oxy, such a poly(oxyalkyl) portion preferably comprising a poly(oxyethylene) group or a poly(oxyethylene)-co-poly(oxypropylene)copolymer group; formylalkyl; aminoalkyl; active esters, for example, succinimidoxycarbonyl; active anhydrides and mixed anhydrides; active carbonates such as arylcarbonatoaryl, alkylcarbonatoaryl, arylcarbonatoalkyl, and alkylcarbonatoalkyl, and the aryl groups of which are preferably comprised of a six membered ring containing electron withdrawing substituents such as, for example, nitro and halogen, and optionally containing water solubilizing groups such as a sulfonate salt; sulfhydryl; sulfhydrylalkyl; thioalkylcarbonylaminoalkyloxy; maleimidoalkylcarbonylaminoalkyloxy; azido; iodoalkylcarbonylamino; amidatoalkylamino; and amidatoarylalkylamino.

The reactive functional group copolymers, such as those listed above, may be of any appropriate length. For example, copolymers may include from 2 to 1000 monomeric units (e.g. 2 to 1000 carbon atoms in an alkyl or alkylene polymer, 2 to 1000 monomeric oxyalkylene units in a poly(oxyethylene)-co-poly(oxypropylene) copolymer group, or an aryloxycarbonyloxyalkyloxy; aryloxycarbonyl(polyoxyalkyl) oxy). In other embodiments, the copolymers may include from 2 to 100 monomeric units or 2 to 20 monomeric units.

The crosslinking agents, reactions, and functional reactive groups set forth above are equally applicable to reactions designed to attach the metal nanoparticles to additional compounds or compositions as set forth herein.

In addition to crosslinking between different organic substituents covalently bound to the same metal core, different organic substituents attached to different metal cores may also be crosslinked. This process leads to two or more metal nanoparticles that are covalently linked together. The covalently linked nanoparticles may be referred to herein as metal polynanoparticles.

In some embodiment, where the organic substituent is substantially water soluble, the metal nanoparticle is substantially water soluble.

Thus, in some embodiments the metal nanoparticles form a portion of a polymer. The metal nanoparticles may be incorporated within an existing polymer or may be employed in synthesizing a polymer. For example, in some embodiments, a metal nanoparticle may be incorporated within an existing polyethylene, polyisoprene, butadiene derived, Sorbothane® (e.g. high density polyurethane) or nitrile butadiene derived (e.g. rubber) product (e.g. gloves) or may be added via chemical addition during a polymerization reaction used to form the rubber product. The polymer may be of any appropriate size or length. In some cases, the polymer contains over 10,000,000 monomeric units (i.e. an ultra high molecular weight polymer). In related embodiments, the polymer includes at least 100,000 monomeric units. In some embodiments, the polymer includes at least 1,000 monomeric units.

III. Metal Nanopowders

In another aspect, a metal nanopowder is provided. A nanopowder is an assembly of a plurality of nanoparticles. In some embodiments, the nanopowder is in at least approximately dry form. The metal nanopowder provided herein includes a plurality of the metal nanoparticles described in the previous section entitled Metal Nanoparticles. Thus, the characteristics described above for metal nanoparticles are equally applicable to the metal nanoparticles that fowl the metal nanopowders described herein.

The plurality of nanoparticles that form the metal nanopowder are typically substantially monodisperse. The phrase "substantially monodisperse," as used herein, refers to a plurality of objects in which a defined portion of particles have a defined size dimension within a defined range or limit. In some embodiments, at least 50% of the metal nanoparticles forming the metal nanopowder are less than 1 µm in length in all dimensions. In some embodiments, at least 50% of the metal nanoparticles forming the metal nanopowder are less than 200 nm in length in all dimensions. In some embodiments, at least 50% of the metal nanoparticles forming the metal nanopowder are less than 100 nm in length in all dimensions. In some embodiments, at least 50% of the metal nanoparticles forming the metal nanopowder are less than 50 nm in length in all dimensions. In other embodiment, at least 50% of the metal nanoparticles forming the metal nanopowder are less than 25 nm in length in all dimensions. In some embodiments, at least 50% of the metal nanoparticles forming the metal nanopowder are less than 10 nm in length in all dimensions. In some embodiments, at least 50% of the metal nanoparticles forming the metal nanopowder are less than 5 nm in length in all dimensions. In some embodiments, at least 50% of the metal nanoparticles forming the metal nanopowder are less than 3 nm in length in all dimensions. In some embodiments, at least 50% of the metal nanoparticles forming the metal nanopowder are from about 1 µm to about 3 nm in length in all dimensions. In some embodiments, at least 50% of the metal nanoparticles forming the metal nanopowder are from about 200 nm to about 5 nm in length in all dimensions. In some embodiments, at least 50% of the metal nanoparticles forming the metal nanopowder are from about 100 nm to about 10 nm in length in all dimensions. In some embodiments, at least 50% of the metal nanoparticles forming the metal nanopowder are from about 50 nm to about 25 nm in length in all dimensions. In some embodiments, at least 50% of the metal nanoparticles forming the metal nanopowder are from about 50 nm to about 10 nm in length in all dimensions.

In some embodiments, at least 60% of the metal nanoparticles forming the metal nanopowder are less than 1 µm in length in all dimensions. In some embodiments, at least 60% of the metal nanoparticles forming the metal nanopowder are less than 200 nm in length in all dimensions. In some embodiments, at least 60% of the metal nanoparticles forming the metal nanopowder are less than 100 nm in length in all dimensions. In some embodiments, at least 60% of the metal nanoparticles forming the metal nanopowder are less than 50 nm in length in all dimensions. In other embodiment, at least 60% of the metal nanoparticles forming the metal nanopowder are less than 25 nm in length in all dimensions. In some embodiments, at least 60% of the metal nanoparticles forming the metal nanopowder are less than 10 nm in length in all dimensions. In some embodiments, at least 60% of the metal nanoparticles forming the metal nanopowder are less than 5 nm in length in all dimensions. In some embodiments, at least 60% of the metal nanoparticles forming the metal nanopowder are less than 3 nm in length in all dimensions. In some embodiments, at least 60% of the metal nanoparticles forming the metal nanopowder are from about 1 µm to about 3 nm in length in all dimensions. In some embodiments, at least 60% of the metal nanoparticles forming the metal nanopowder are from about 200 nm to about 5 nm in length in all dimensions. In some embodiments, at least 60% of the metal nanoparticles forming the metal nanopowder are from about 100 nm to about 10 nm in length in all dimensions. In some embodiments, at least 60% of the metal nanoparticles forming the metal nanopowder are from about 50 nm to about 25 nm in length in all dimensions. In some embodiments, at least 60% of the metal nanoparticles forming the metal nanopowder are from about 50 nm to about 10 nm in length in all dimensions.

In some embodiments, at least 70% of the metal nanoparticles forming the metal nanopowder are less than 1 µm in length in all dimensions. In some embodiments, at least 70% of the metal nanoparticles forming the metal nanopowder are less than 200 nm in length in all dimensions. In some embodiments, at least 70% of the metal nanoparticles forming the metal nanopowder are less than 100 nm in length in all dimensions. In some embodiments, at least 70% of the metal nanoparticles forming the metal nanopowder are less than 50 nm in length in all dimensions. In other embodiment, at least 70% of the metal nanoparticles forming the metal nanopowder are less than 25 nm in length in all dimensions. In some embodiments, at least 70% of the metal nanoparticles forming the metal nanopowder are less than 10 nm in length in all dimensions. In some embodiments, at least 70% of the metal nanoparticles forming the metal nanopowder are less than 5 nm in length in all dimensions. In some embodiments, at least 70% of the metal nanoparticles forming the metal nanopowder are less than 3 nm in length in all dimensions. In some embodiments, at least 70% of the metal nanoparticles forming the metal nanopowder are from about 1 µm to about 3 nm in length in all dimensions. In some embodiments, at least 70% of the metal nanoparticles forming the metal nanopowder are from about 200 nm to about 5 nm in length in all dimensions. In some embodiments, at least 70% of the metal nanoparticles forming the metal nanopowder are from about 100 nm to about 10 nm in length in all dimensions. In some embodiments, at least 70% of the metal nanoparticles forming the metal nanopowder are from about 50 nm to about 25 nm in length in all dimensions. In some embodiments, at least 70% of the metal nanoparticles forming the metal nanopowder are from about 50 nm to about 10 nm in length in all dimensions.

In some embodiments, at least 80% of the metal nanoparticles forming the metal nanopowder are less than 1 µm in length in all dimensions. In some embodiments, at least 80% of the metal nanoparticles forming the metal nanopowder are less than 200 nm in length in all dimensions. In some embodiments, at least 80% of the metal nanoparticles forming the metal nanopowder are less than 100 nm in length in all dimensions. In some embodiments, at least 80% of the metal nanoparticles forming the metal nanopowder are less than 50 nm in length in all dimensions. In other embodiment, at least 80% of the metal nanoparticles forming the metal nanopowder are less than 25 nm in length in all dimensions. In some embodiments, at least 80% of the metal nanoparticles forming the metal nanopowder are less than 10 nm in length in all dimensions. In some embodiments, at least 80% of the metal nanoparticles forming the metal nanopowder are less than 5 nm in length in all dimensions. In some embodiments, at least 80% of the metal nanoparticles forming the metal nanopowder are less than 3 nm in length in all dimensions. In some embodiments, at least 80% of the metal nanoparticles forming the metal nanopowder are from about 1 µm to about 3 nm in length in all dimensions. In some embodiments, at least 80% of the metal nanoparticles forming the metal nanopowder are from about 200 nm to about 5 nm in length in all dimensions. In some embodiments, at least 80% of the metal nanoparticles forming the metal nanopowder are from about 100 nm to about 10 nm in length in all dimensions. In some embodiments, at least 80% of the metal nanoparticles forming the metal nanopowder are from about 50 nm to about 25 nm in length in all dimensions. In some embodiments, at least 80% of the metal nanoparticles forming the metal nanopowder are from about 50 nm to about 10 nm in length in all dimensions.

In some embodiments, at least 90% of the metal nanoparticles forming the metal nanopowder are less than 1 µm in length in all dimensions. In other embodiments, at least 90% of the metal nanoparticles forming the metal nanopowder are less than 200 nm in length in all dimensions. In some embodiments, at least 90% of the metal nanoparticles forming the metal nanopowder are less than 100 nm in length in all dimensions. In some embodiments, at least 90% of the metal nanoparticles forming the metal nanopowder are less than 50 nm in length in all dimensions. In other embodiment, at least 90% of the metal nanoparticles forming the metal nanopowder are less than 25 nm in length in all dimensions. In some embodiments, at least 90% of the metal nanoparticles forming the metal nanopowder are less than 10 nm in length in all dimensions. In some embodiments, at least 90% of the metal nanoparticles forming the metal nanopowder are less than 5 nm in length in all dimensions. In some embodiments, at least 90% of the metal nanoparticles forming the metal nanopowder are less than 3 nm in length in all dimensions. In some embodiments, at least 90% of the metal nanoparticles forming the metal nanopowder are from about 1 µm to about 3 nm in length in all dimensions. In some embodiments, at least 90% of the metal nanoparticles forming the metal nanopowder are from about 200 nm to about 5 nm in length in all dimensions. In some embodiments, at least 90% of the metal nanoparticles forming the metal nanopowder are from about 100 nm to about 10 nm in length in all dimensions. In some embodiments, at least 90% of the metal nanoparticles forming the metal nanopowder are from about 50 nm to about 25 nm in length in all dimensions. In some embodiments, at least 90% of the metal nanoparticles forming the metal nanopowder are from about 50 nm to about 10 nm in length in all dimensions.

In some embodiments, at least 95% of the metal nanoparticles forming the metal nanopowder are less than 1 µm in length in all dimensions. In other embodiments, at least 95% of the metal nanoparticles forming the metal nanopowder are less than 200 nm in length in all dimensions. In some embodiments, at least 95% of the metal nanoparticles forming the metal nanopowder are less than 100 nm in length in all dimensions. In some embodiments, at least 95% of the metal nanoparticles forming the metal nanopowder are less than 50 nm in length in all dimensions. In other embodiment, at least 95% of the metal nanoparticles forming the metal nanopowder are less than 25 nm in length in all dimensions. In some embodiments, at least 95% of the metal nanoparticles forming the metal nanopowder are less than 10 nm in length in all dimensions. In some embodiments, at least 95% of the metal nanoparticles forming the metal nanopowder are less than 5 nm in length in all dimensions. In some embodiments, at least 95% of the metal nanoparticles forming the metal nanopowder are less than 3 nm in length in all dimensions. In some embodiments, at least 95% of the metal nanoparticles forming the metal nanopowder are from about 1 µm to about 3 nm in length in all dimensions. In some embodiments, at least 95% of the metal nanoparticles forming the metal nanopowder are from about 200 nm to about 5 nm in length in all dimensions. In some embodiments, at least 95% of the metal nanoparticles forming the metal nanopowder are from about 100 nm to about 10 nm in length in all dimensions. In some embodiments, at least 95% of the metal nanoparticles forming the metal nanopowder are from about 50 nm to about 25 nm in length in all dimensions. In some embodiments, at least 95% of the metal nanoparticles forming the metal nanopowder are from about 50 nm to about 10 nm in length in all dimensions.

In other embodiments, 100% of the metal nanoparticles forming the metal nanopowder are less than 1 µm in length in all dimensions. In other embodiments, 100% of the metal nanoparticles forming the metal nanopowder are less than 200 nm in length in all dimensions. In some embodiments, 100% of the metal nanoparticles forming the metal nanopowder are less than 100 nm in length in all dimensions. In some embodiments, 100% of the metal nanoparticles forming the metal nanopowder are less than 50 nm in length in all dimensions. In other embodiment, 100% of the metal nanoparticles forming the metal nanopowder are less than 25 nm in length in all dimensions. In some embodiments, 100% of the metal nanoparticles forming the metal nanopowder are less than 10 nm in length in all dimensions. In some embodiments, 100% of the metal nanoparticles forming the metal nanopowder are less than 5 nm in length in all dimensions. In some embodiments, 100% of the metal nanoparticles forming the metal nanopowder are less than 3 nm in length in all dimensions. In some embodiments, 100% of the metal nanoparticles forming the metal nanopowder are from about 1 µm to about 3 nm in length in all dimensions. In some embodiments, 100% of the metal nanoparticles forming the metal nanopowder are from about 200 nm to about 5 nm in length in all dimensions. In some embodiments, 100% of the metal nanoparticles forming the metal nanopowder are from about 100 nm to about 10 nm in length in all dimensions. In some embodiments, 100% of the metal nanoparticles forming the metal nanopowder are from about 50 nm to about 25 nm in length in all dimensions. In some embodiments, 100% of the metal nanoparticles forming the metal nanopowder are from about 50 nm to about 10 nm in length in all dimensions.

In some embodiments, the metal nanopowders include metal nanoparticles in which two or more different organic substituents on the metal core are crosslinked. In other embodiments, the metal nanopowders include one or more metal polynanoparticles, as described above.

IV. Radiation Shields

In another aspect, radiation shields are provided. A "radiation shield," as used herein, refers to a devise placed between an article (e.g. an inanimate object such as a radiation sensitive device or material), a biological subject (e.g. a mammal such as a human) or biomatter (e.g. tissue derived from a mammal such as a human) and a radiation source in order to block or reduce radiation exposure of the article, subject or biomatter from the radiation source. Examples of non-living or inanimate objects articles include, but are not limited to, a human cadaver, electronic componentry for use in land, sea, air, and space based applications such as satellites, military and defense systems, energy monitoring systems, public and private sector research equipment, medical measurement equipment, and so forth.

The radiation shields provided herein may block or reduce radiation exposure across the entire spectrum of radiation, including for example radiation emanating from medical equipment, military weaponry, and cell phones. In some embodiments, the radiation shields provided herein may alternatively block or reduce radiation exposure across a select or particular spectrum range as a high-pass, low-pass, band-pass or selective notch filter with varying orders of attenuation including, but not limited to, first, second, third and forth order as well as non-linear attenuation-energy/frequency relationships. The radiation shields provided herein include a metal nanoparticle as described above in the section entitled Metal Nanoparticles, the characteristics of which are equally applicable to the metal nanoparticles used in the radiation shields provided herein. Thus, in some embodiments the radiation shield includes a metal nanopowder as described in the section entitled Metal Nanopowders, the characteristics of which are equally applicable to the metal nanoparticles used in the radiation shields provided herein. The smaller diameter of the particle may, in some embodiments, represents a higher effective attenuation ability to radiation relative to the packing density, or mass, of the final attenuation material and/or product.

In some embodiments, the radiation shield includes a metal nanoparticle including a metal core and an outer layer encompassing the metal core. The outer layer includes a plurality of organic substituents bonded (e.g. covalently bonded) to the metal core. The metal nanoparticle is less than 1 µm (e.g. 200 nm) in length in all dimensions. Other size limited embodiments of the metal nanoparticle are described above and are equally applicable to the metal nanoparticles that at least partially form the radiation shields described herein.

In some embodiments, the radiation shield is lead-free (i.e. either does not include any lead or does not include an amount of lead effective in reducing or blocking radiation).

The radiation shield may be a personal radiation shield. A personal radiation shield refers to a devise placed between a subject (e.g. a human) and a radiation source in order to block or reduce radiation exposure of the subject from the radiation source. The personal radiation shield may be used to shield radiation (i.e. reduce radiation exposure) from any appropriate radiation source, including for example a cell phone, a medical device, or equipment used in aerospace applications (e.g. shielding from assorted E&M in aerospace and space applications for both material (electronics, mechanical) protection as well as protection of humans and biomatter).

The radiation shield may be provided in a wide variety of forms, including for example, a blanket, head covering, foot covering, hand covering, an undergarment, an injection molded product, or an extruded product. The radiation shield (especially a personal radiation shield) may include a nonwoven material, a fiber material, a film, a filament, or a woven material.

V. Additional Metal Nanoparticle and Nanopowder Utilities

In addition to radiation shields, the nanoparticles and a nanopowders disclosed herein may be used in a wide range of devices. For example, the nanoparticles and nanopowders may be incorporated into abrasive solids, ceramics, surface coatings, intrinsic dielectrics, and devices for ballistic protection (e.g. bullet proof vests). The nanoparticles and nanopowders may be pressed, modified, or otherwise integrated into a fabric or other existing structures (such as Kevlar, fiberglass, etc.).

Resulting products containing the nanoparticles and/or nanopowders can be used as an additive for trauma reduction.

Polymers (e.g. rubber) products containing the nanoparticles or nanopowders may be molded into functional and non-functional goods such as gloves, gas masks, gasketting for assorted garments and other sealing and non-sealing applications. The materials may be advantageous for applications such as patient protection during CT-scan procedures.

Products containing the nanoparticles or nanopowders are additionally advantageous for use in production equipment (extrusion, etc.) to lessen strain, abrasion, and overall wear and tear. The small nanoparticle size also broadens the size-regime over which extrusion, spinners and spinnerets, etc. can be utilized for pre and post production.

In addition, the nanoparticles or nanopowders may be added to creams, gels, liquid supports, etc. such as sunscreen.

In another aspect, a method is provided for making a metal nanoparticle. The method allows for a substantial increase in overall relevant packing density, here increasing the overall active particle surface area as a functional of mass density. The provided method allows for nanoparticles having an exceptionally high surface area to volume (volume here is proportional to mass) thereby increasing the overall radiation attenuation capabilities as an overall function of mass.

VI. Methods of Making Metal Nanoparticles

In another aspect, a method is provided for making a metal nanoparticle or a plurality of metal nanoparticles. In some embodiments, the method for making a plurality of metal nanoparticles comprises the step of contacting a metal with a diazonium compound substituted with an organic substituent. In some embodiments, the method for making a plurality of metal nanoparticles comprises the step of allowing the metal to react with the diazonium compound thereby forming a metal nanoparticle (or a plurality of nanoparticles, such as a nanopowder). In some embodiments, the metal nanoparticle (or the plurality of metal nanoparticles) includes a metal core and an outer layer encompassing the metal core. In some embodiments, the outer layer includes a plurality of the organic substituents bonded (e.g. covalently bonded) to the metal core. In some embodiments, the method for making a plurality of metal nanoparticles comprises the steps of (a) contacting a metal with a diazonium compound substituted with an organic substituent; and (b) allowing the metal to react with the diazonium compound thereby forming a plurality of metal nanoparticles wherein the plurality of metal nanoparticles comprises a metal core and an outer layer encompassing the core, the outer layer comprising a plurality of organic substituents covalently bonded to the metal core, wherein at least 50% of the plurality of metal nanoparticles are less than 1 µm in length in all dimensions. Thus, in some embodiments, the characteristics of the metal nanoparticles set forth above are equally applicable to the metal nanoparticles and plurality of metal nanoparticles made using the methods set forth herein.

In some embodiments, the method for making a plurality of metal nanoparticles includes the step of contacting a metal with a plurality of diazonium compounds substituted with an organic substituent. In some embodiments, the method for making a plurality of metal nanoparticles comprises the step of allowing the metal to react with the plurality of diazonium compounds thereby forming a metal nanoparticles (or a plurality of nanoparticles, such as a nanopowder). In some embodiments, the method for making a plurality of metal nanoparticles comprises the steps of (a) contacting a metal with a plurality of diazonium compounds substituted with an organic substituent; and (b) allowing the metal to react with the plurality of diazonium compounds thereby forming a plurality of metal nanoparticles wherein the plurality of metal nanoparticles comprises a metal core and an outer layer encompassing the core, the outer layer comprising a plurality of organic substituents covalently bonded to the metal core, wherein at least 50% of the plurality of metal nanoparticles are less than 1 µm in length in all dimensions. Thus, in some embodiments, the characteristics of the metal nanoparticles set forth above are equally applicable to the metal nanoparticles and plurality of metal nanoparticles made using the methods set forth herein.

The metal may be in any appropriate form. In some embodiments, the metal is a bulk material of any appropriate dimension. Thus, the methods provided herein allow one of skill to proceed from the macroscopic to microscopic level thereby increasing the surface area of the subject metal. The increased surface area provides advantages for a wide array of applications, including for example increased packing density and thus superior radiation attenuation.

In some embodiments, the metal is in the form of metal granules. Where the metal is in the form of metal granules, the method results in a plurality of metal nanoparticles. In some embodiments, the method for making a plurality of metal nanoparticles comprises the step of contacting metal granules (or a plurality of metal granules) with a diazonium compound substituted with an organic substituent. In some embodiments, the method for making a plurality of metal nanoparticles comprises the step of allowing the metal granules (or the plurality of metal granules) to react with the diazonium compound thereby forming a metal nanoparticle (or a plurality of nanoparticles, such as a nanopowder). In some embodiments, each of the metal nanoparticles includes a metal core and an outer layer encompassing the metal core. In some embodiments, the outer layer includes a plurality of the organic substituents bonded (e.g. covalently bonded) to the metal core. In some embodiments, the method for making a plurality of metal nanoparticles comprises the steps of (a) contacting metal granules with a diazonium compound substituted with an organic substituent; and (b) allowing the metal granules to react with the diazonium compound thereby forming a plurality of metal nanoparticles wherein the plurality of metal nanoparticles comprises a metal core and an outer layer encompassing the core, the outer layer comprising a plurality of organic substituents covalently bonded to the metal core, wherein at least 50% of the plurality of metal nanoparticles are less than 1 µm in length in all dimensions. Thus, in some embodiments, the characteristics of the metal nanoparticles set forth above are equally applicable to the metal nanoparticles made using the methods set forth herein.

In some embodiments, the method for making a plurality of metal nanoparticles includes the step of contacting metal granules (or a plurality of metal granules) with a plurality of diazonium compounds substituted with an organic substituent. In some embodiments, the method for making a plurality of metal nanoparticles comprises the step of allowing the metal granules (or the plurality of metal granules) to react with the plurality of diazonium compounds thereby forming a metal nanoparticles (or a plurality of nanoparticles, such as a nanopowder). In some embodiments, the method for making a plurality of metal nanoparticles comprises the steps of (a) contacting metal granules with a plurality of diazonium compounds substituted with an organic substituent; and (b) allowing the metal granules to react with the plurality of diazonium compounds thereby forming a plurality of metal nanoparticles wherein the plurality of metal nanoparticles comprises a metal core and an outer layer encompassing the core, the outer layer comprising a plurality of organic substituents covalently bonded to the metal core, wherein at least 50% of the plurality of metal nanoparticles are less than 1 µm in length in all dimensions. Thus, in some embodiments, the characteristics of the metal nanoparticles set forth above are equally applicable to the metal nanoparticles and plurality of metal nanoparticles made using the methods set forth herein.

The plurality of metal nanoparticles produced using this method are substantially monodisperse. The monodispersion characteristics of metal nanopowders described above the section entitled Metal Nanopowders are equally applicable to the of the plurality of metal nanoparticles made by the methods disclosed herein. Although those characteristics will not be repeated in full here, it is noted that in some embodiments, at least 50% of the plurality of metal nanoparticles produced by methods set forth herein are less than 1 µm in length in all dimensions. In other embodiments, at least 50% of the plurality of metal nanoparticles produced by methods set forth herein are less than 200 nm in length in all dimensions. In other embodiments, at least 60% of the plurality of metal nanoparticles produced by methods set forth herein are less than 100 nm in length in all dimensions. In other embodiments, at least 70% of the plurality of metal nanoparticles produced by methods set forth herein are less than 100 nm in length in all dimensions. In other embodiments, at least 80% of the plurality of metal nanoparticles produced by methods set forth herein are less than 100 nm in length in all dimensions. In other embodiments, at least 90% of the plurality of metal nanoparticles produced by methods set forth herein are less than 100 nm in length in all dimensions. In other embodiments, at least 95% of the plurality of metal nanoparticles produced by methods set forth herein are less than 100 nm in length in all dimensions. In other embodiments, 100% of the plurality of metal nanoparticles produced by methods set forth herein are less than 100 nm in length in all dimensions. In other embodiments, at least 90% of the plurality of metal nanoparticles produced by methods set forth herein is less than 50 nm in length in all dimensions. In other embodiments, at least 90% of the plurality of metal nanoparticles produced by methods set forth herein is less than 25 nm in length in all dimensions. In other embodiments, at least 90% of the plurality of metal nanoparticles produced by methods set forth herein is less than 10 nm in length in all dimensions. In other embodiments, at least 90% of the plurality of metal nanoparticles produced by methods set forth herein is less than 5 nm in length in all dimensions. at least 90% of the plurality of metal nanoparticles produced by methods set forth herein is less than 3 nm in length in all dimensions. In some embodiments, at least 60% of the metal nanoparticles produced by methods set forth herein are from about less than 1 µm to about less than 3 nm in length in all dimensions. In some embodiments, at least 60% of the metal nanoparticles produced by methods set forth herein are from about less than 200 nm to about less than 5 nm in length in all dimensions. In some embodiments, at least 60% of the metal nanoparticles produced by methods set forth herein are from about less than 100 nm to about less than 10 nm in length in all dimensions. In some embodiments, at least 60% of the metal nanoparticles produced by methods set forth herein are from about less than 50 nm to about less than 25 nm in length in all dimensions. In some embodiments, at least 60% of the metal nanoparticles produced by methods set forth herein are from about less than 50 nm to about less than 10 nm in length in all dimensions.

In some embodiments, the metal and/or the metal core includes or consists entirely of a metal selected from the group consisting of germanium, antimony, polonium, tellurium, scandium, yttrium, lanthanum, actinium, titanium, zirconium, hafnium, rutherfordium, niobium, dubnium, chromium, molybdenum, seaborgium, manganese, technetium, rhenium, bohrium, ruthenium, osmium, hassium, cobalt, rhodium, iridium, meitnerium, palladium, platinum, darmstadtium, copper, silver, roentgenium, zinc, cadmium, mercury, indium, gallium, thallium, ununbium, tungsten, gold, aluminum, bismuth, iron, vanadium, nickel, palladium, tin, lead, tantalum, and uranium. In some embodiments, the metal is tungsten, germanium, gold, aluminum, bismuth, iron, vanadium, silver, nickel, palladium, tin, lead, tantalum, copper, or uranium. In some embodiments, the metal is gold. In some embodiments, the metal is silver. In some embodiments, the metal is aluminum. In some embodiments, the metal is iron. In some embodiments, the metal is iron-oxide. In some embodiments, the metal is copper. In some embodiments, the metal is germanium. In some embodiments, the metal is tungsten. In some embodiments, the metal and the metal core consist of tungsten. In some embodiments, the metal granules and the metal core include or consist entirely of tungsten. In some embodiments, the metal granules and the metal core consist of tungsten.

In some embodiments, where the metal is in the from a metal granules, the metal granules are less than about 100 μm in length in all dimensions. In other embodiments, the metal granules are less than about 50 μm in length in all dimensions. In other embodiments, the metal granules are less than about 25 μm in length in all dimensions. In other embodiments, the metal granules are less than about 10 μm in length in all dimensions. In some embodiments, the metal granules are from about 1 μm to about 3 nm in length in all dimensions. In some embodiments, the metal granules are from about 200 nm to about 5 nm in length in all dimensions. In some embodiments, the metal granules are from about 100 nm to about 10 nm in length in all dimensions. In some embodiments, the metal granules are from about 50 nm to about 25 nm in length in all dimensions. In some embodiments, the metal granules are from about 50 nm to about 10 nm in length in all dimensions.

The nature of the interaction between the organic substituents and the metal core are described above in the context of metal nanoparticles and are equally applicable to the metal nanoparticles synthesized using the methods described herein. For example, the plurality of organic substituents may be covalently bonded to the metal core through a carbon-metal covalent bond.

Moreover, the characteristics of the organic substituents described above in the section entitled Metal Nanoparticles are equally applicable to the plurality of organic substituents that form part of the metal nanoparticles synthesized using the methods described herein. For example, the plurality of organic substituents may be selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In some embodiments, a diazonium compound used in the methods presented herein has the formula $R^{17}$—$N_2^+$ where $R^{17}$ is an organic substituent (as described above in the section entitled Metal Nanoparticles). Thus, $R^{17}$ may be a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl. $R^{17}$ may also have the structure of Formula (I) above. In some embodiments, $R^{17}$ is a substituted or unsubstituted porphyrin moiety optionally bond with a porphyrin metal.

The specific diazonium compound used will depend upon the characteristics desired for the organic substituents covalently bonded to the metal core. In some embodiments, the organic substituent of the diazonium compound will be limited to increase effective mass loading, lower reagent cost, and/or attain higher chemical stability. Thus, in some embodiments the organic substituent is a substituted or unsubstituted $C_1$-$C_{20}$ alkyl, a substituted or unsubstituted 2 to 20 membered heteroalkyl, a substituted or unsubstituted $C_3$-$C_8$ cycloalkyl, a substituted or unsubstituted 3 to 8 membered heterocycloalkyl, a substituted or unsubstituted monocyclic aryl, or a substituted or unsubstituted monocyclic heteroaryl.

In other embodiments, the organic substituent is a substituted or unsubstituted $C_1$-$C_8$ alkyl, a substituted or unsubstituted 2 to 8 membered heteroalkyl, a substituted or unsubstituted $C_5$-$C_7$ cycloalkyl, a substituted or unsubstituted 5 to 7 membered heterocycloalkyl, a substituted or unsubstituted monocyclic aryl, or a substituted or unsubstituted monocyclic heteroaryl.

In embodiments related to the previous two paragraphs, each substituted group described above for the organic substituent is substituted with least one size-limited substituent group. Alternatively, at least one or all of these groups are substituted with at least one lower substituent group.

In some embodiments, the organic substituent has the structure of Formula (I). In related embodiments, $L^1$ is an unsubstituted alkylene. In further related embodiments, $L^1$ is an unsubstituted $C_1$ to $C_{10}$ alkylene.

In some embodiments, the organic substituent is butyric acid. Thus, in some embodiments, the diazonium compound is diazobutyric acid (e.g. γ-diazobutyric acid).

The diazonium compound may be synthesized using any appropriate method. In some embodiments, an organic substituent having an amino group (also referred to herein as an amine-diazonium precursor) is reacted with an alkali nitrite salt, such as a cesium or sodium nitrite. For example, where the amine-diazonium precursor has the formula $H_2N$-$L^1$-COOH, the diazonium compound having the formula $N_2^+$-$L^1$-COOH may be formed by contacting the amine-diazonium precursor with a nitrite salt (e.g. sodium nitrite). In some embodiments, the amine-diazonium precursor is γ-amino butyric acid, the nitrite salt is sodium nitrite, and the diazonium compound is diazo-butyric acid.

In some embodiments, the molar ratio of the amine-diazonium precursor (e.g. γ-amino butyric acid) to the nitrite salt is from about 1:1 to about 1:2. In some embodiments, the molar ratio of the amine-diazonium precursor (e.g. γ-amino butyric acid) or the nitrite salt is about 1:1.1.

In some embodiments, the reaction of the amine-diazonium precursor with the alkali nitrite salt occurs in the presence of a metal (e.g. metal granules). Without being bound by any particular mechanism of action, it is believed that the diazonium compounds, once formed, etch the metal into small metal particles thereby exposing increased metal surface area to the metal reaction with the diazonium compound to form the carbon metal bond between the organic substituent and the metal core. In other embodiments, the concentration of the amine-diazonium precursor (e.g. γ-amino butyric acid) is no more than about 0.1 M. In other embodiment, the concentration of the alkali nitrite salt (e.g. sodium nitrite) is no more than about 0.1 M. In some embodiments, the concentration of the metal (e.g. tungsten) is no more than about 0.02 M.

In some embodiments, the molar ratio of the amine-diazonium precursor or the alkali nitrite salt to the metal at the start of the reaction is from about 1:1 to about 10:1. In other embodiments, the molar ratio of the amine-diazonium precursor or the alkali nitrite salt to the metal at the start of the reaction is from about 2:1 to about 7:1. In other embodiments, the molar ratio of the amine-diazonium precursor or the alkali nitrite salt to the metal at the start of the reaction is from about 3:1 to about 5:1. In other embodiments, the molar ratio of the amine-diazonium precursor or the alkali nitrite salt to the metal at the start of the reaction is about 4:1 or about 5:1.

In some embodiments, where the amine-diazonium precursor is combined with the nitrite salt and metal, the amine-diazonium precursor is first added to an acidic solution. Where the amine-diazonium precursor is water soluble, the acidic solution is an aqueous acidic solution.

The aqueous solution including the amine-diazonium precursor may be separately combined with the metal prior to contact with the alkali nitrite salt. Thus, in some embodiments, an aqueous acidic solution including the amine-diazonium precursor and the metal is contacted with an aqueous solution including the alkali nitrite salt (i.e. an aqueous sodium nitrite salt solution). The metal nanoparticle thus formed may precipitate out of solution, typically by adjusting the pH to the appropriate level using an appropriate base.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The referenced patents, patent applications, and scientific literature, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Moreover, the characteristics of the metal nanoparticles, including the organic substituents, recited in the methods (e.g. the methods of making the metal nanoparticles) are equally applicable to the compositions (e.g. the metal nanoparticles, the metal nanopowders and the radiation shields) and vice versa. And the characteristics of the metal nanoparticles, including the organic substituents, recited in a particular composition (e.g. the metal nanoparticles) are equally applicable to the other compositions (e.g. the metal nanopowders and the radiation shields).

As can be appreciated from the disclosure above, the present invention has a wide variety of applications. While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention. The invention is further illustrated by the following examples, which are only illustrative and are not intended to limit the definition and scope of the invention in any way.

VII. Examples

The below examples are meant to illustrate specific embodiments of the methods and compositions described herein and should not be construed as limiting the scope of the invention in any way.

Example 1

Production of Tungsten Nanoparticles

Molar Masses: Tungsten: ~184 g/mol; GABA (γ-amino butyric acid): ~103 g/mol; Sodium Nitrite: ~69 g/mol.

Concentrated (10 M) HCl was added to water thereby diluting to a concentration of 2M. For every 1 gram of tungsten, 109 ml of water and 27 ml of concentrated HCl was used. A total volume of ~10 ml was measured with a graduated cylinder or volumetric pipette, and placed in a 50 ml Erlenmeyer flask containing a Teflon coated stir bar.

GABA was added to the diluted HCl solution to a concentration of 0.2 M, being measured with a 0.0001 g accuracy scale, and chilled, with an ice-salt bath, to a temperature below 0° C. For every 1 grams of tungsten, 2.8 grams of GABA was used.

Fine grain metallic tungsten was added to the GABA/HCl—$H_2O$ solution at a concentration of 0.04 M (here 1 gram).

In a separate container, water was measured to a volume of approximately ⅕ that of the GABA solution and placed in a flask or beaker. Sodium nitrite was added to a concentration slightly larger than 1 M (i.e. 1.1 M), also being measured with a 0.0001 g accuracy scale, and chilled in the same ice-salt bath. For every 1 gram of tungsten, 1.9 grams of sodium nitrite was added to 27.2 ml of water.

While chilling, the sodium nitrite solution was slowly added to the GABA/tungsten solution while stirring vigorously in a well-ventilated area. Stirring was continued until nitrous gas evolution was no longer observed.

Figure 2:
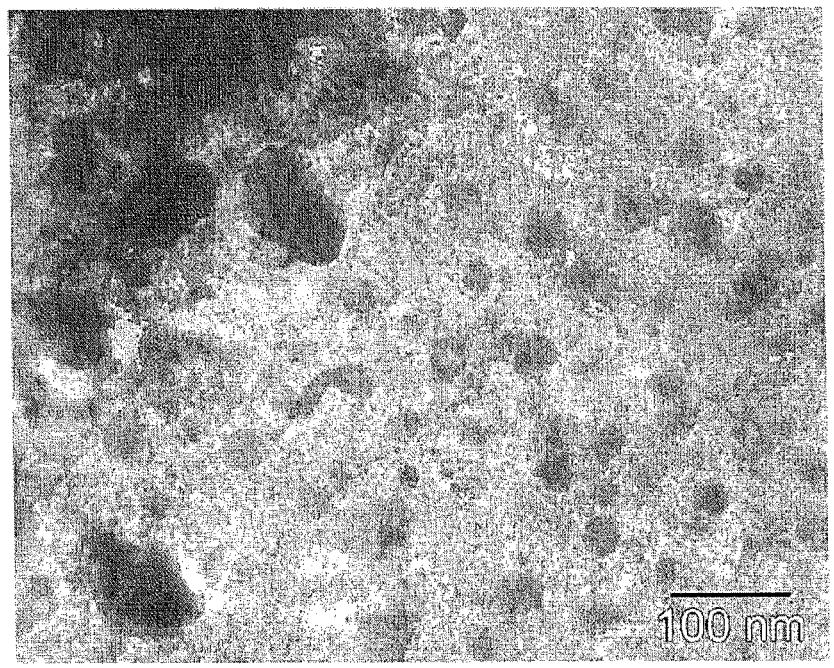
FIG. 2 depicts a TEM image of another form of a metal powder fabricated according to the invention. Details are described in Example 1.
Figure 3:
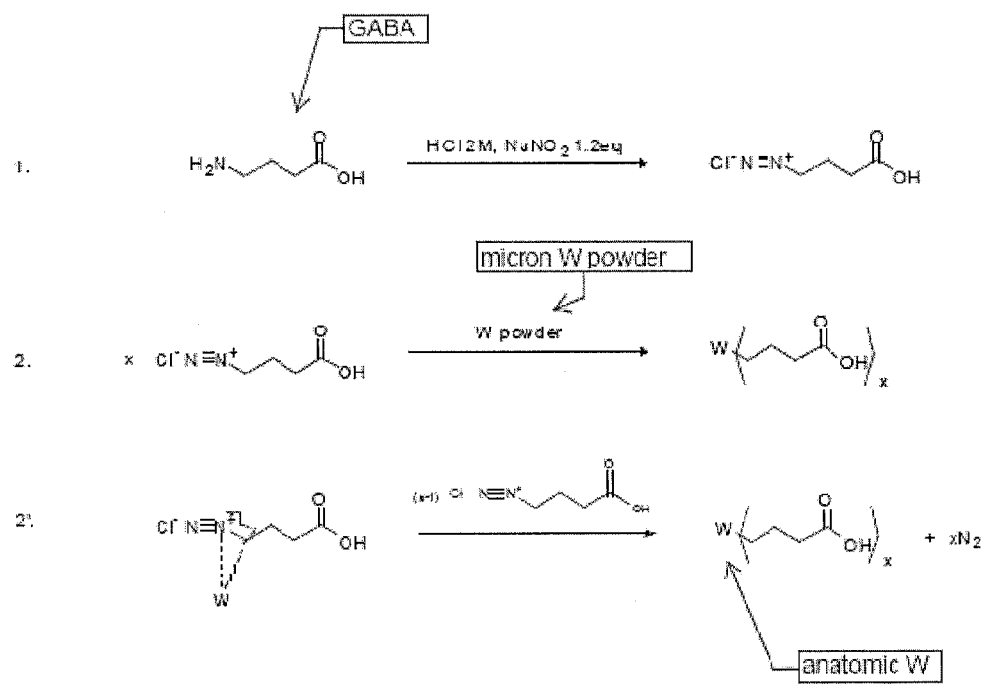
FIG. 3 depicts a reactionscheme for producing tungsten nanoparticles according to a method of the invention and as described in Example 1.

The solution was decanted, leaving behind any un-reacted tungsten. NaOH was added to a 2 M equivalent. For every 1 gram of tungsten, 11 grams of NaOH solid was added slowly and the tungsten nanoparticle precipitate was collected. The product tungsten nanoparticles are illustrated in FIGS. 1 and 2. A preferred reaction scheme is shown in FIG. 3.

In sum, for every 1 gram of tungsten processed, the following amounts were used: 2.8 grams GABA in 136 ml of 2 M HCl solution (along with the 1 gram of tungsten); 1.9 grams Sodium Nitrite in 27.2 ml of water; 11 grams of NaOH.

Some experiments were performed at a 5:1 molar ratio of GABA and sodium nitrite to tungsten in a 2 M HCl solution. The maximum preferred concentration of the GABA is about 0.1 M, as with the sodium nitrite, making the maximum concentration of tungsten about 0.02 M.

The exemplary method of producing tungsten nanoparticles described above produced nanoparticles of less than 200 nm (nano to colloidal) particles with a self-assembled monolayer (SAM) of butyric acid molecules.

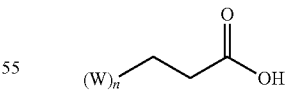

The tungsten-carbon bond is known to be especially strong and stable and the carboxylic group, facing outwards from the particle, is a well-characterized functional group that lends itself well to polymerization as well as solubility in polar solvents.

Without being bound by theory, the process is believed to occur by rapidly etching sub-5 μm particles by rapidly exposing them to the highly reactive γ-diazobutyric acid, formed by reacting γ-aminobutyric acid with sodium nitrite in a 1 to 2 M HCl aqueous solution:

The highly reactive diazo species etch the tungsten into water-soluble molecular species, in the above example, sub-200 nm in scale based on various sources. Approximately 1.1 molar equivalents of sodium nitrite relative to the γ-aminobutyric acid was used to ensure full and rapid conversion. Full solubilization of the initially macroscopic tungsten particles has been obtained, e.g., at a diazo-W ratio of approximately 5:1. Although production of the diazo species in the presence of tungsten powder will likely push this value closer to the stoichiometrically expected value of 1:1.

Without being bound by theory, it is assumed that the majority of the excess diazo species reactive with each other before being able to combine with the tungsten due to both: a) the zero oxidation state/steric hindrance of the tungsten surface and; b) the exceptionally low stability and high reactivity associated with diazo-alkane species (they are very short lived and not available commercially.) It is also possible that the diazo species react with the carboxylic end-group of other molecules competitively.

One of skill in the art will appreciate that the process described above will work with any diazo species. For the purposes of radiation opacity, however, a smaller diazo species is preferred due to the higher effective mass loading, lower reagent cost, and the typically higher chemical stability associated with the shorter chain alkanes.

Example 2

Melt Mixing and Post-Processing of Nanoparticles in Polymer

Figure 4A:
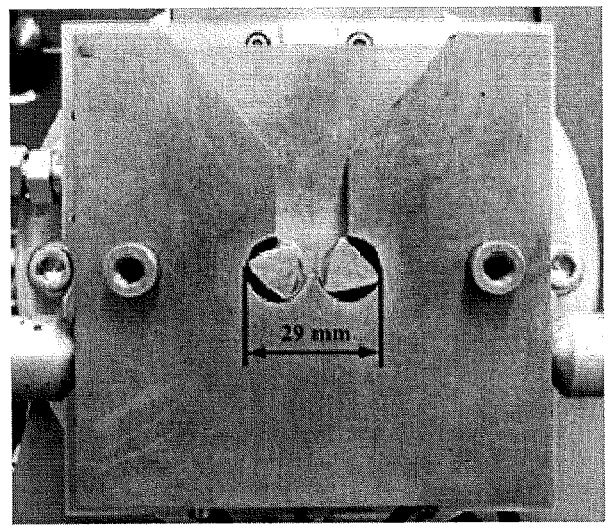
FIG. 4 depicts photographs of miniature mixtures used for melting experiments: (A) MBM and (B) APAM. Details are described in Example 2.
Figure 4B:
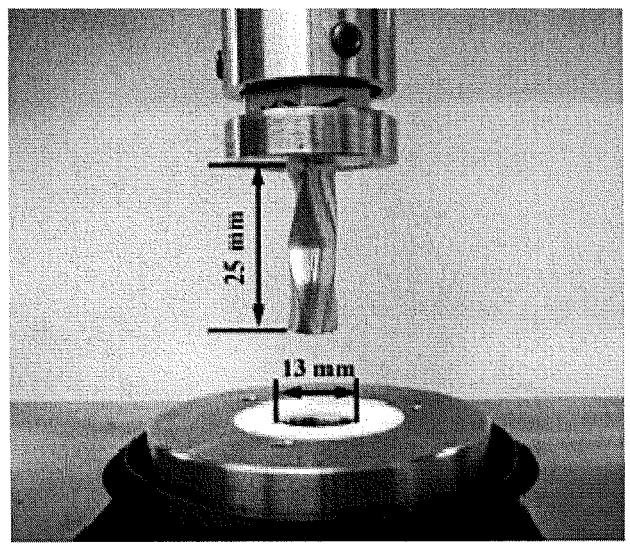

Applicants melt mixed polymer and tungsten nanoparticles (or nanopowder) at 200° C. in their custom made miniature mixers, Miniature Batch Mixer (MBM; FIG. 4A) and the Alberta Polymer Assymmeetric Minimixer (APAM; FIG. 4B). The effects of nanoparticle concentration, mixing time, mixing temperature and mixer type were investigated for the mixing experiments. It was found that the MBM is easier than the APAM for feeding and processing the materials. The maximum loading of the tungsten particles was found to be around 85 wt % in the MBM. The Thermogravimetric Analysis (TGA) showed that the weight loss of the tungsten powder started at 130° C., however, the process was slow and the total weight loss at 550° C. was only 5.3%. On the other hand, the TGA thermograms of the composites indicated that there were two transition temperatures, which were around 384° C. and 470° C., respectively. It was also found that the residues of the composites were much less compared to the total amount of tungsten powders used in the mixing experiments. Selected composites were molded in a hot press into a rectangular sheet (L×W×H 42×25×1 mm) at 180° C. Details are provided below.

(A) Materials

Materials used for the mixing and post-processing of nanoparticles in polymer experiments were provided by Radiation Shield Technologies (RST, Coral Gables, Fla. 33134, USA). The materials were polymer resin and tungsten nanoparticles (or nanopowder). The polymer pellets (flat and round in shape) are transparent and elastic at room temperature. The typical processing temperature for the polymer resin is 180-200° C. The tungsten particles have a light yellowish color, which are fluffy in air. The density of the resin is 0.9 g/cm$^3$ and the bulk density of the powder is around 1.5 g/cm$^3$ at 25° C.

(B) Melt Mixing

FIG. 3 shows the two miniature mixers used for melt mixing of the polymer and the nanoparticles. The first mixer, MBM, is a 3 cm$^3$ miniature batch mixer (FIG. 4a), consisting of two counter-rotating roller blades in a dual-cylindrical cavity. The second miniature mixer, ADAM (FIG. 4b), is composed of a unique asymmetric rotor and a cylindrical chamber with a capacity of 2.2 cm$^3$. The fill volume of the polymer and the particles in the mixers was 75 vol %, which was based on an estimation density of the resin, 0.8 g/cm$^3$ at 200° C. and the bulk density of the particles, 1.5 g/cm$^3$. Table 1 lists the experiments performed in the mixers.

TABLE 1

| | Melt Mixing Experiments | | | | | | |
|---|---|---|---|---|---|---|---|
| Exp. # | Tungsten Powder (vol %) | Tungsten Powder (wt %) | Mixer Type | Rotation Speed (RPM) | Mixing Time (min) | Mixing Temp. (° C.) | Note |
| 1 | 25 | 38.5 | MBM | 100 | 10 | 200 | Effect on conc. |
| 2 | 50 | 65.2 | MBM | 100 | 10 | 200 | |
| 3 | 60 | 73.8 | MBM | 100 | 10 | 200 | |
| 4 | 75 | 84.9 | MBM | 100 | 10 | 200 | |
| 5 | 50 | 65.2 | MBM | 100 | 20 | 200 | Effect of mixing time |
| 6 | 50 | 65.2 | MBM | 50 | 20 | 200 | |
| 7 | 50 | 65.2 | MBM | 100 | 10 | 220 | Effect of mixing temp. |
| 8 | 50 | 65.2 | MBM | 50 | 10 | 220 | |
| 9 | 50 | 65.2 | APAM | 50 | 20 | 200 | Different Type of Mixer |
| 10 | 50 | 65.2 | APAM | 100 | 10 | 200 | |
| 11 | 50 | 65.2 | MBM | 50 | 20 | 200 | Repeat #6 |
| 12 | 50 | 65.2 | MBM | 100 | 10 | 200 | Repeat #2 |
| 13 | 50 | 65.2 | APAM | 100 | 10 | 200 | Repeat #10 |

Before feeding the materials into the mixers, the appropriate mass of polymer pellets and the nanoparticles was weighed and then the two materials were premixed with a small spatula. The feeding of the materials through the chute to the MBM was slow, and took around 1.5 to 2.0 min. After mixing at the specified temperature, rotation speed and mixing time, the composites were quickly frozen in liquid nitrogen for at least fifteen minutes and then collected for further characterizations and tests. As the concentration of the nanoparticle increased, the composite product became less elastic. At around 85 wt %, the materials appeared to be quite rigid and the exchange of materials between the two rotors in MBM was difficult. A flat stagnant surface was observed at this concentration when the chute ram of the MBM was opened, i.e., the materials were stuck at the top of the rotors. For the mixing experiments done in the MBM, the effects of other experimental parameters, such as the mixing time, temperature and rotation speed, did not show much difference for the appearance of the final product. However, when changing the mixer from MBM to APAM, the initial feeding of materials into the APAM cup became much more difficult because of the small volume of the cup and the bulkiness of the powders.

The maximum load of the nanoparticles was also studied by increasing the concentration stepwise in the MBM. For step 1, one 50 vol % composite was mixed at 200° C., 100 rpm and 10 min (same condition as run #2 in Table 1). This first composite was cut into 2-3 mm pellets after being frozen in the liquid nitrogen. These pellets were then mixed with tungsten powder in step 2 to increase loading to 70 vol %. For step 3, the sample collected from step 2 was further mixed with the nanoparticles to an increased concentration of 80 vol %, which is equivalent to 88.2 wt % of nanopowder. The mixing for step 3 was poor since no material exchange between the rotors was observed, and the product from step 3 showed a mixture of powdery and cohesive texture. No higher loading experiment could be done above this concentration. Based on this set of experiments, the maximum loading of the tungsten powder in the MBM was 88.2 wt %.

(C) TGA Analysis

Figure 5:
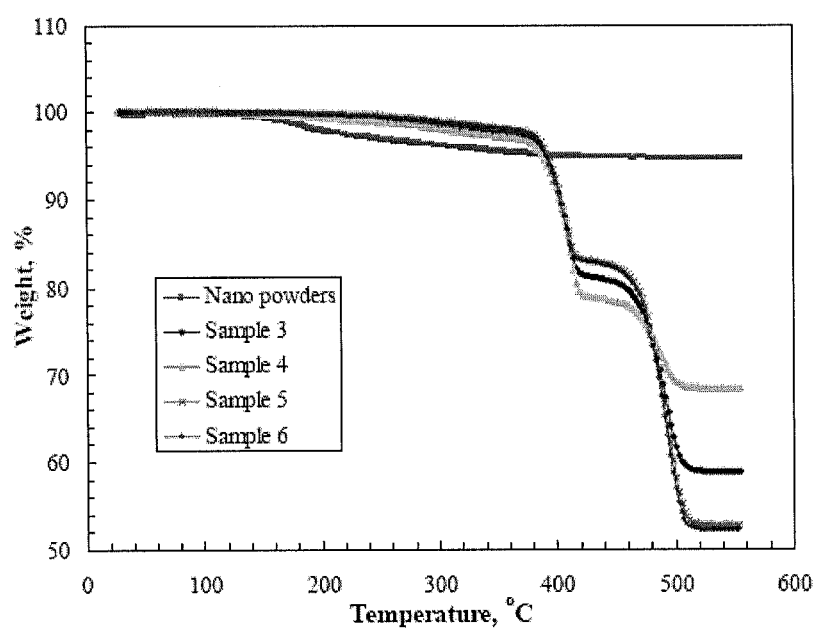
FIG. 5 depicts thermograms of tungsten powder and composites prepared from MBB (Sample #3, #4, #5, and #6). Details are described in Example 2.
Figure 6:
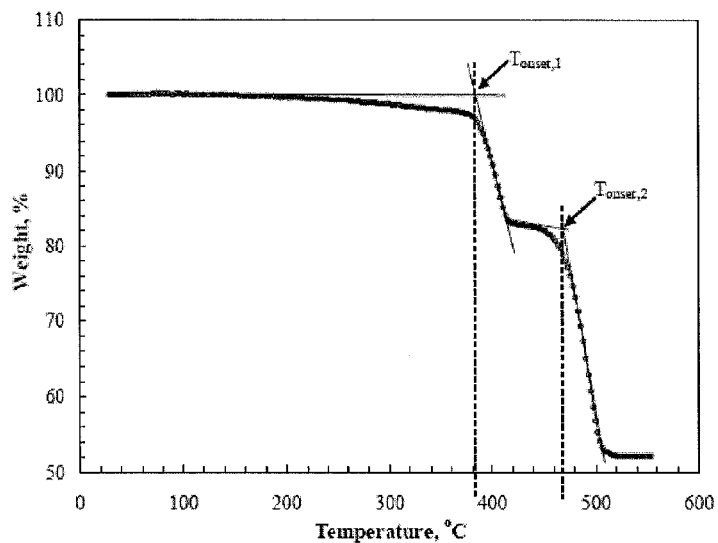
FIG. 6 depicts determination of weight loss onset temperature from a thermogram, as described in Example 2.

TGA analysis was performed with STP 409PC LUXX themogravimetric analyzer (NETZSCH). The experiments were run from 30° C. to 550° C. at 10° C./min under nitrogen environment. FIG. 5 shows the thermograms of the tungsten powders and selected composites, Sample #4, #5, #6 and #7 (note that the sample number corresponds to the melt mixing experiments shown in Table 1). The tungsten nanopowder shows gradual reduction in weight with increasing temperature, and the residual mass at 550° C. is 94.7%. However, for the composites, there are two transition temperatures for weight loss as seen in the thermograms. Here, the transition temperature is defined as the onset temperature of weight loss, which is obtained from the thermogram as illustrated in FIG. 6.

Table 2 summarizes the residue mass and the onset temperature of weight loss. The two onset temperatures for the composites studied are similar, which are around 384° C. and 470° C., respectively. The TGA thermograms for sample #5 and #6 are very close, in which the tungsten contents are the same, but the rotation speed is different for these two samples, indicating that there is little effect of rotation speed on the final products. On the other hand, the total weight loss of the composites is closely related to the nanoparticle concentration, the higher the load, the less the weight loss (sample #4<sample #3<sample #5~sample #6). Assuming that the polymers were all burned at 550° C., the difference between the total weight loss and the polymer 5 for the sample #4, #3, #5 and #6 is 16.7%, 15.0%, 12.5% and 13.1%, respectively, which are much higher than that for the pure tungsten nanopowder.

TABLE 2

Summary of TGA Results

| Sample | Tungsten Powder (wt %) | Polymer (wt %) | Residual Mass at 550° C. (%) | Total Weight Loss (%) | Difference of Total Weight Loss and Polymer (%) | Onset Temp. (° C.) $T_{onset, 1}$ | Onset Temp. (° C.) $T_{onset, 1}$ |
|---|---|---|---|---|---|---|---|
| Tungsten Nanopowder | 100 | 0 | 94.7 | 5.3 | 5.3 | 141 | |
| 3 | 73.8 | 26.2 | 58.8 | 41.2 | 15.0 | 385 | 472 |
| 4 | 84.9 | 15.1 | 68.2 | 31.8 | 16.7 | 386 | 470 |
| 5 | 65.2 | 34.8 | 52.7 | 47.3 | 12.5 | 384 | 468 |
| 6 | 65.2 | 34.8 | 52.1 | 47.9 | 13.1 | 382 | 468 |

(D) Hot Press Molding

Figure 7:
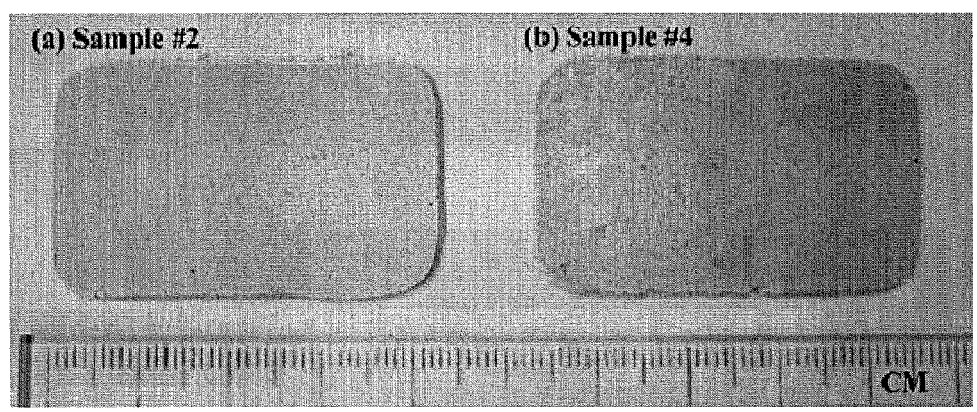
FIG. 7 depicts a photograph of the compression molded sample (a) #2 and (b) #4, as described in Example 2.

Ten selected composites (sample #1-#7, #9, #10 and #13) from Table 1 were compression molded with a Carver Laboratory Press into rectangular sheets with dimensions: L×W×H 42×25×1 mm. The composites collected after the mixing experiments were first cut into 2-3 mm small pieces, and the small pieces were weighed to have enough material for the mold size and then these pieces were placed in the mold. The press was electrically heated to 180° C. and the sample sheet was made under 7.8 MPa for four minutes, and then immediately cooling down with water for ten minutes. FIG. 7 shows the photograph of the compression molded sheets of sample #2 (65.2 wt % powder) and #4 (84.9 wt % powder).

(E) Perspective

The polymer and tungsten nanopowder were melt mixed at 200° C. in MBM and APAM. The MBM was used for most mixing experiments since it was easier for feeding the materials. In the experiments described herein, the maximum loading of the tungsten particle was found to be around 85 wt % in the MBM either by adding the materials together or by feeding the materials in successive steps. The Thermogravimetric Analysis (TGA) of the tungsten nanopowder and four selected composite samples (#3, #4, #5 and #6) showed that the residual mass at 550° C. were 94.7%, 58.8%, 68.2%, 52.7% and 52.1%, respectively. The TGA thermograms of the composites had two transition temperatures and the difference between the total weight loss and the polymer for the sample #3, #4, #5 and #6 was 15.0%, 16.7%, 12.5% and 13.1%, respectively, which were much higher than that for the tungsten nanopowder alone, 5.3%. Selected composite sheets were compression molded at 180° C. in a hot press.

What is claimed is:

1. A method of making tungsten nanoparticles comprising:
   (a) contacting tungsten with a diazonium compound substituted with an organic substituent; and
   (b) allowing the tungsten to react with the diazonium compound thereby forming tungsten nanoparticles wherein each of said tungsten nanoparticles comprises a tungsten core bonded to an outer layer of said organic substituent.

2. The method of claim 1, wherein at least 50% of said tungsten nanoparticles are less than 1 μm in length in all dimensions.

3. The method of claim 1, wherein at least 70% of said tungsten nanoparticles are less than 100 nm in length in all dimensions.

4. The method of claim 1, wherein at least 80% of said tungsten nanoparticles are less than 100 nm in length in all dimensions.

5. The method of claim 1, wherein at least 90% of said tungsten nanoparticles are less than 100 nm in length in all dimensions.

6. The method of claim 1, wherein at least 95% of said tungsten nanoparticles are less than 100 nm in length in all dimensions.

7. The method of claim 1, wherein 100% of said tungsten nanoparticles are less than 100 nm in length in all dimensions.

8. The method of claim 1, wherein said organic substituents are covalently bonded to said tungsten core.

9. The method of claim 1, wherein said organic substituents are selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

10. The method of claim 1, wherein said plurality of organic substituents are selected from the group consisting of consisting of $R^1$-substituted or unsubstituted alkyl, $R^1$-substituted or unsubstituted heteroalkyl, $R^1$-substituted or unsubstituted cycloalkyl, $R^1$-substituted or unsubstituted heterocycloalkyl, $R^1$-substituted or unsubstituted aryl, and $R^1$-substituted or unsubstituted heteroaryl;
   wherein $R^1$ is halogen, —CN, —S(O)$_n$R$^2$, —NR$^3$R$^4$, —C(O)R$^5$, —NR$^6$—C(O)R$^7$, —NR$^8$—C(O)—OR$^9$, —C(O)NR$^{10}$R$^{11}$, —NR$^{12}$S(O)$_2$R$^{13}$, —OR$^{14}$, —S(O)$_2$NR$^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl, wherein n is an integer from 0 to 2; and
   $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl.

11. The method of claim 1, wherein said organic substituents have the formula:

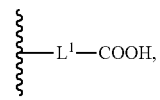

wherein
   $L^1$ is $R^1$-substituted or unsubstituted alkylene, $R^1$-substituted or unsubstituted heteroalkylene, $R^1$-substituted or unsubstituted cycloalkylene, $R^1$-substituted or unsubstituted heterocycloalkylene, $R^1$-substituted or unsubstituted arylene, and $R^1$-substituted or unsubstituted heteroarylene;
   $R^1$ is halogen, —CN, —S(O)$_n$R$^2$, —NR$^3$R$^4$, —C(O)R$^5$, —NR$^6$—C(O)R$^7$, —NR$^8$—C(O)—OR$^9$, —C(O)NR$^{10}$R$^{11}$, —NR$^{12}$S(O)$_2$R$^{13}$, —OR$^{14}$, —S(O)$_2$NR$^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl, wherein n is an integer from 0 to 2,
   $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

12. The method of claim 11, wherein $L^1$ is $R^1$-substituted or unsubstituted alkylene.

13. The method of claim 11, wherein $L^1$ is $R^1$-substituted or unsubstituted $C_1$-$C_{20}$ alkylene.

14. The method of claim 11, wherein $L^1$ is $R^1$-substituted or unsubstituted $C_1$-$C_{10}$ alkylene.

15. The method of claim 11, wherein $L^1$ is $R^1$-substituted or unsubstituted $C_1$-$C_5$ alkylene.

16. The method of claim 11, wherein $L^1$ is $R^1$-substituted or unsubstituted $C_1$-$C_3$ alkylene.

17. The method of claim 11, wherein $L^1$ is unsubstituted $C_1$-$C_3$ alkylene.

18. The method of claim 1, further comprising a plurality of organic substituents bonded to said tungsten core.

19. The method of claim 1, wherein at least 90% of said tungsten nanoparticles is less than 50 nm in length in all dimensions.

20. The method of claim 1, wherein at least 90% of said tungsten nanoparticles is less than 25 nm in length in all dimensions.

21. The method of claim 1, wherein at least 90% of said tungsten plurality of metal nanoparticles is less than 10 nm in length in all dimensions.

22. The method of claim 1, wherein at least 90% of said tungsten nanoparticles is less than 5 nm in length in all dimensions.

23. The method of claim 1, wherein at least 90% of said tungsten nanoparticles is less than 3 nm in length in all dimensions.

* * * * *